United States Patent [19]
Joutel et al.

[11] Patent Number: 5,616,462
[45] Date of Patent: Apr. 1, 1997

[54] METHOD FOR THE DIAGNOSIS OF CADASIL

[75] Inventors: Anne M. G. Joutel; Marie-Germaine M. Bousser; Elisabeth A. Tournier-Lasserve, all of Paris, France

[73] Assignee: L'Assistance Publique—Hospitaux de Paris, Paris, France

[21] Appl. No.: 202,920

[22] Filed: Feb. 28, 1994

[51] Int. Cl.⁶ .............................. C12Q 1/68; C12P 19/34; C07H 21/02; C07H 21/04
[52] U.S. Cl. ........................ 435/6; 435/91.2; 536/23.1; 536/24.3; 536/24.33
[58] Field of Search ..................... 435/6, 91.2; 536/23.1, 536/24.3, 24.33

[56] References Cited

PUBLICATIONS

Joutel et al. Nature Genetics 5(1): 40–45 1993.
Bousser et al. Stroke 25: 704–707 1993.
Olsson, Brain Pathology 4: 101–103 1994.
Hovatta et al. Genomics 23: 707–709 1994.
Joutel et al. Am. J. Hum. Genet. 55:1166–1172 1994.
Sabbadini et al. Brain 118: 207–215 1995.
Verin et al. Neurology 44: A288 1994.
Tournier-Lasserve et al., Nature Genetics 3:256–259 1993.
Joutel et al, Am. J. Human Genetics, 55:1166–1172, 1994.
Genetic Heterogeneity of Familial Hemiplegic Migraine.
Tournier-Lasserve et al, Stroke 22:1297–1302*, 1991.

Primary Examiner—W. Gary Jones
Assistant Examiner—Dianne Rees
Attorney, Agent, or Firm—Larson & Taylor

[57] ABSTRACT

Genotypic diagnosis of CADASIL for symptomatic or at risk individuals or fetuses belonging to a family suspected of being affected by CADASIL is carried out by detecting DNA polymorphisms genetically linked to the mutated gene responsible for CADASIL, these DNA polymorphisms being located in the genetic interval of the chromosome 19 flanked by the microsatellites D19S221 and D19S215 and including these microsatellites.

6 Claims, 6 Drawing Sheets

METHOD FOR THE DIAGNOSIS OF CADASIL

The present invention relates to a method for the diagnosis of Cerebral Autosomal Dominant Arteriopathy with Subcortical Infarcts and Leukoencephalopathy (CADASIL).

BACKGROUND OF THE INVENTION

Stroke is the third leading cause of death and the first cause of acquired physical or cognitive impairment in developed countries. Strokes are ischaemic in 80% of cases and the leading causes are atheroma and cardiac emboli. But despite extensive investigation, up to 40% of cases remain without definite actiology.

Familial causes of stroke have recently been identified, such as MELAS and homocystinuria. Since 1977, nine unrelated families have been reported with a new mendelian syndrome that leads to stroke. Recently a pedigree was reported, the large size of which allowed the precise definition of the clinical, neuro-imaging and genetic parameters of this disease (Tournier-Lasserve et al, Stroke, 1991, 22, 1297–1302, Tournier-Lasserve et al, Nature Genetics, 1993, 3, 256–259). This condition is characterized by recurrent subcortical ischaemic strokes and dementia. It is underlaid by a cerebral non-atherosclerotic, non-amyloid angiopathy affecting mainly the small arteries penetrating the white matter and basal ganglia. All reported families share strikingly similar clinical, neuro-imaging and pathological features. The acronym CADASIL (cerebral autosomal dominant arteriopathy with subcortical infarcts and leukoencephalopathy) is used.

SUMMARY OF THE INVENTION

Genetic linkage analysis conducted on 2 large CADASIL pedigrees assigned the CADASIL locus to chromosome 19 and multilocus analysis with the location scores method established the best estimate for the location of the gene within a 14 cM interval bracketed by D19S221 and D19S215 loci. (Nature Genetics, 1993, 3, 256–259 and Nature Genetics, 1993, 5, 40–46).

All CADASIL families tested until now are genetically homogenous and map to the same previously defined interval on chromosome 19.

The invention has several objects:

One object of the invention is to provide a method for diagnosing CADASIL within an affected family.

Another object of the invention is to provide a method to identify the CADASIL families to be analyzed for predictive testing by genetic linkage analysis with chromosome 19 markers.

It is yet another object of invention to provide a method for predictive testing in an "at risk" individual within a CADASIL family.

Another object of the invention is to provide a method for prenatal diagnosis of CADASIL.

These objects are attained by a method for genotypic diagnosis of CADASIL by searching for the presence of a mutated gene responsible for the disease, comprising the search for the presence of a mutation responsible for CADASIL on chromosome 19, in the region of it comprised between the microsatellites D19S221 and D19S215, notably within a family suspected to be affected by CADASIL, within an at risk individual member of an affected family or within an at risk foetus.

Preferably, this method is based on genetic linkage analysis of human samples belonging to the members of the affected families to be tested. The first step is to establish linkage of the disease gene responsible for the disease present in the family with the CADASIL locus. Linkage analysis is conducted on families whose structure is suitable for such analysis, namely families comprising multiple individuals whose clinical and cerebral magnetic resonance imaging (MRI) status (healthy or affected) has been unambiguously established (see Nature Genetics, 1993, 3, 256–259). Disease status for linkage analysis is based on the cerebral MRI data. All clinically affected members have an abnormal cerebral MRI. At risk asymptomatic individuals whose MRI shows the same lesions as the ones observed in clinically affected subjects are considered as affected. Asymptomatic offspring of an affected individual having a normal MRI is considered as having an unknown status when aged below 35 year old.

Genetic linkage analysis is preferably conducted with a set of highly polymorphic DNA markers (microsatellites flanking highly polymorphic CA or GATA repeats) spanning the most likely location intervals of CADASIL.

Markers are selected to give the best informativity for a given family. Markers located on both sides of the gene increase the accuracy of the diagnosis and permit the reduction of the risks of false diagnosis in case of recombination. These markers include D19S221, D19S179, D19S226, D19S252, D19S253, D19S244, D19S415, D19S199, D19S215.

These microsatellites are described in the microsatellites Genethon map (Weissenbach J. & al., Nature 359, 794–801, 1992 which is incorporated therein by reference) as well as in J. Weber et al, Am. J. Hum. Gen. 1993, 53, 1079–1095. The oligonucleotide sequences serving as primers, which are specific for each microsatellite, are available in the Genome Data Bank (Accessing GDB™ and OMIM™ at John Hopkins University, Baltimore, Md., USA).

The preferred method consists of hybridization of selected primers to the DNA to be tested, followed by DNA amplification by Polymerase Chain Reaction amplification. Preferably, the polymorphic amplified fragments, so called amplimers, are then separated according to their size by electrophoresis on acrylamide denaturing gels, blotted on nylon membranes and hybridized with CA 12 mer or GATA 5 mer radiolabelled probes. Data obtained from autoradiographs are computed and Lod-score calculations are carried out using the M-LINK program (Lathrop et al, P.N.A.S., 1984, 81, 3443–3446.). Based on MRI data, penetrance has been established to be complete after 35 year old (see above).

The assertion of linkage or absence of linkage is derived from statistical analysis, a lod-score above 3 establishing unambiguous linkage of the disease gene to the tested marker. A lod-score value of 3 is in fact needed only when the prior probability of linkage between a disease gene and a marker is no more than random, which is not anymore the case for CADASIL. The strictness of this criterion should be soon decreased according to the prior probability values observed in on going epidemiological studies.

CADASIL is a recently identified hereditary condition responsible for stroke and genotypic diagnosis provides a tool which allows clinicians to identify this disease and avoid differential diagnosis with other white matter disorders.

In a second step, genotypic analysis can be used for predictive testing of asymptomatic at risk individuals, members of an affected family. Using linked polymorphic markers, a DNA based carrier risk can be calculated using the MLINK program (Lathrop et al, P.N.A.S., 1984, 81, 3443–3446.). The same method can be used for prenatal carrier-risk diagnosis.

Thus, the preferred general method with respect to the kind of diagnosis comprises hybridizing DNA fragments from an individual with selected primer pairs which hybridize selectively to DNA sequences flanking allelic DNA polymorphisms situated in the said region comprised between the microsatellites D19S221 and D19S215, including the latter, separately amplifying the DNA polymorphisms flanked by the primers thus forming so-called amplimers and analysing these polymorphisms in order to assess the presence or absence of linkage or the DNA polymorphism carrier risk by genetic linkage analysis.

The discovery by the inventors that the CADASIL gene was linked to a specific region of chromosome 19 rendered the principle of a genotypic diagnostic method available. It is evident that from this information and the DNA polymorphisms disclosed that it is easy for the specialist to test other markers which would be tested or discovered later. Additionally, on the basis of the therein-disclosed microsatellites, it is easy to search other polymorphisms which are closer to the gene responsible for CADASIL. The method consists of the search of new polymorphisms which are linked to at least one of the microsatellites disclosed herein. The potential polymorphisms can be then submitted to a linkage analysis in relation with the gene, in order to determine the genetic distances and the Lod Scores.

Therefore, another object of the invention is to propose a method for selecting polymorphisms which are closely related to the gene responsible for CADASIL, wherein, with the aid of DNA probes, one searches for polymorphisms and then one submit these polymorphisms to a linkage analysis with the microsatellite markers D19S221, D19S179, D19S226, D19S252, D19S253, D19S244, D19S415, D19S199, D19S215. Thereafter, one can proceed with a linkage analysis of the selected polymorphisms with respect to the disease gene.

DETAILED SPECIFICATION

Clinical Evaluation

Figure 1:
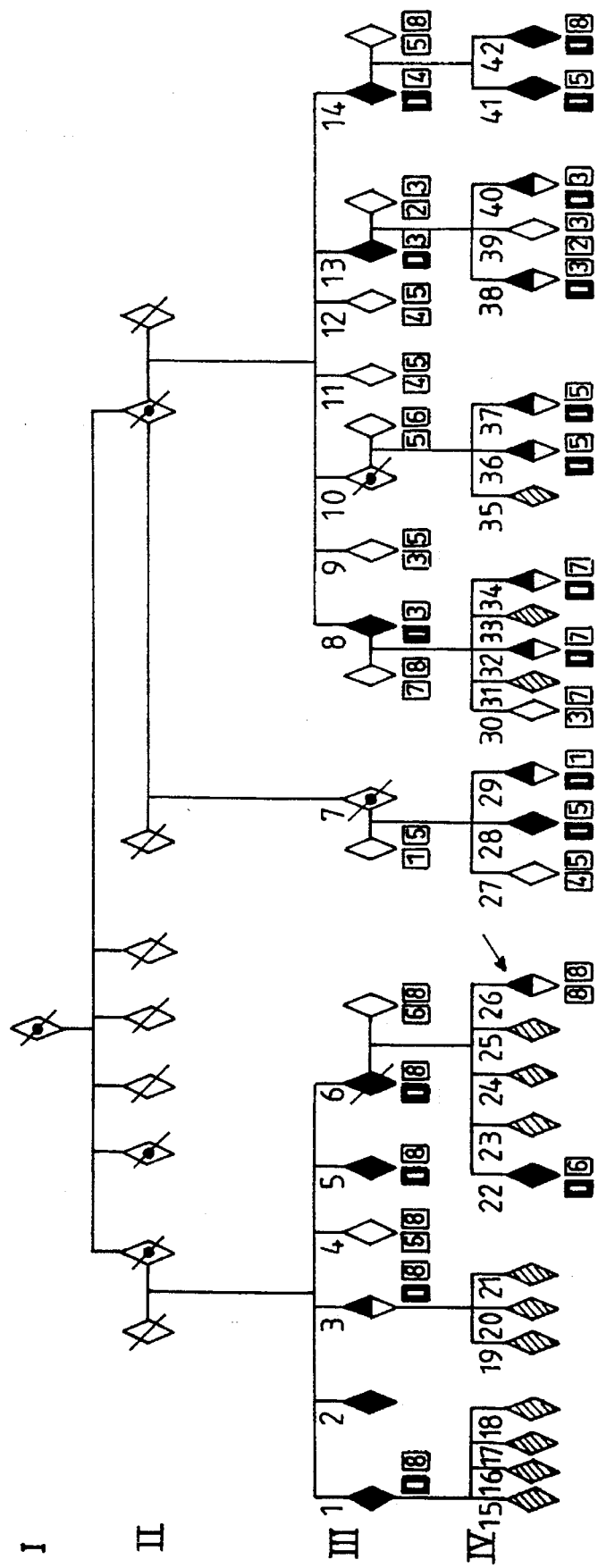
FIG. 1: Details of the D19S226 (AFM 256yc9) genotype in the first CADASIL pedigree (family 1) analysed. The pedigree shown in disguised for reasons of confidentiality and constitutes a simplified version compared to the ones previously reported. For the same reasons, a pair of monozygotic twins was represented as a unique individual. The Roman numbers, on the left side, represent the generations; the numbers above the symbols identify the individuals. The affected subjects are represented by a filled symbol when they have neurological symptoms (filled circle when the symptoms are assumed on the basis of familiar history) and by a half-filled symbol when they have only an abnormal MRI (Magnetic Resonance Imaging). Empty symbols stand for unaffected subjects greater than 35 years of age (assumed based on the absence of neurological signs and a normal MRI) and hatched symbols for unaffected subjects below 35 years of age. The various alleles of AFM 256yc9 are indicated in the boxes. The allele cosegregating with the disease is shadowed. The recombinant affected individual is indicated with an arrow.
Figure 2:
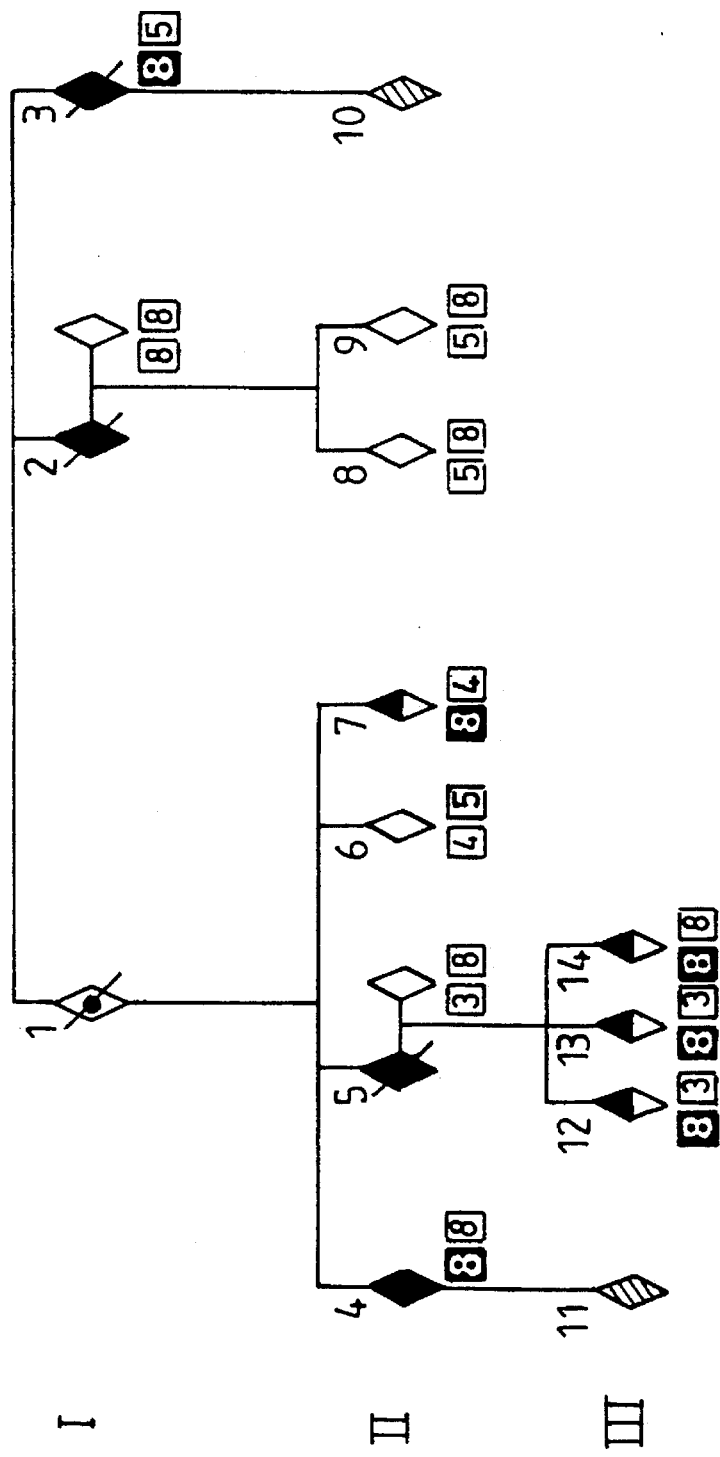
FIG. 2: analogous to FIG. 1 for the second CADASIL pedigree (family 2).

Two unrelated Caucasian families from France were studied (FIG. 1 and 2).

In the first family (family 1), fifty-seven living members were analysed. Eleven patients had suffered recurrent stroke starting at a mean age of 43.3 (28–60 years old). Three of them later developed a pseudobulbar palsy and subcortical dementia. Magnetic resonance imaging (MRI) of the brain showed small, deep and well delineated areas of abnormal signal in all patients (decreased on T1 Weighted images (T1WI), and increased on T2WI), highly suggestive of infarcts. Extensive areas of increased signal were also observed in the hemispheric white matter on T2WI. These areas of increased white matter signal were also present in eight totally asymptomatic subjects (mean age 39 years), each of them having an affected parent. By contrast, such signals were never observed in the offspring of unaffected parents.

The second family (family 2) is unrelated to the first. Among the 14 consenting subjects studied, two had the same clinical presentation of recurrent subcortical ischaemic strokes starting at 42 and 41 years of age, respectively. The same MRI images suggestive of small deep infarcts and leukoencephalopathy were observed in both patients. The white matter disorder was also present on T2WI in four asymptomatic individuals having an affected parent.

Linkage Studies

Lymphoblastoid cell lines were established for all consenting members of the two families. Assuming that the leukoencephalopathy observed on the brain MRI scans represents an early stage of the disease, MRI was performed on all consenting adults aged above 25 years of age, even when clinically healthy. A clearly abnormal brain MRI was observed in 12 healthy individuals, all of whom had an affected parent. They were younger than clinically affected individuals and were considered as asymptomatic carriers. Therefore the disease status for linkage analysis was established on the cerebral MRI data. Asymptomatic offspring of an affected individual having a normal MRI test was considered as uncertain below 35 years old and not analysed, MRI phenotype penetrance was considered as complete above 35 years of age.

Genetic linkage analysis was first performed in family 1. Thirty-four individuals including 26 potentially informative meloses (including all 19 affected individuals) were analysed. Candidate genes coding for various components of the arterial wall, elastin, fibrillins 5 and 15, collagen genes and hexabrachion gene, were tested and excluded. The amyloid precursor protein gene (APP), which is responsible for the haemorrhagic cerebral autosomal dominant angiopathy of Dutch type, was also investigated and excluded ($\theta=0.19$ at $Z=-2$).

Figure 3:
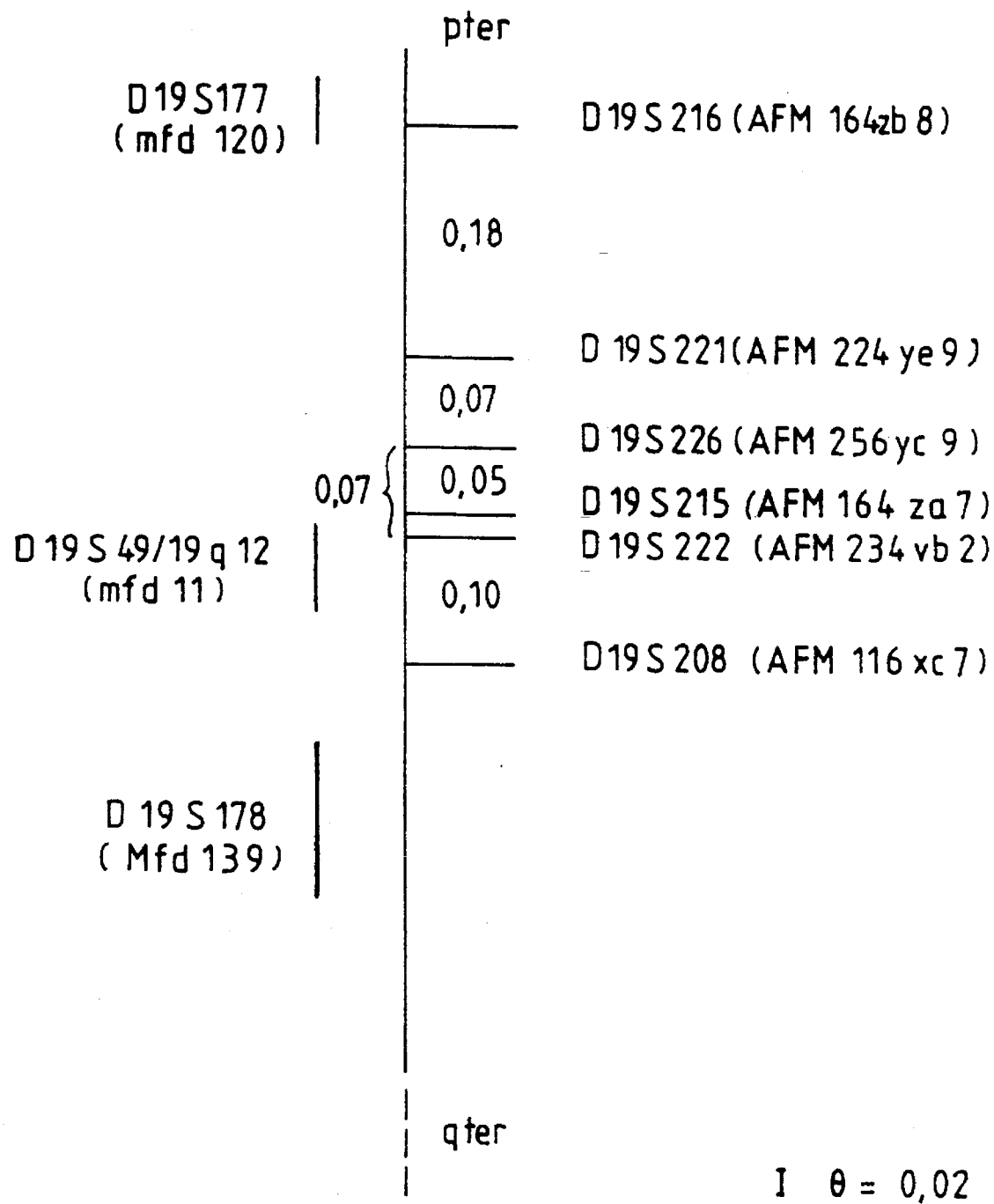
FIG. 3: Genetic regional map of chromosone 19, Critical markers used for linkage analysis are indicated with their respective genetic distances ($\theta$). Map is shown to scale. Approximate location is shown for selected markers from the CEPH database (version 5). The order of the markers was determined as described in Weissenbach, J & al., Nature 359, 794–801(1992).

In the absence of linkage to any of these candidate genes, a sequential study of the whole genome was conducted with anonymous probes. Markers were selected on the basis of their heterozygotic frequency (>60%) and when possible with a genetic distance between them of about 20 centiMorgans (cM). Twenty-five minisatellites VNTRs and 111 $(CA)_n$ microsatellites markers of known chromosomal location were used (see Methodology), An exclusion map for 70% of the genome with the first pedigree (family) was generated and linkage was eventually found between the disease gene and D19S226 (APM 256yc9) on chromosome 19 (FIG. 3 and Table 1). Because founding members of the pedigrees were unavailable for genotyping, the allele's frequency was determined in the CEPH Caucasian reference families and these frequencies were used for pairwise and multipoint linkage analysis. A maximum lod score of 6.34 was obtained at a recombination fraction of $\theta=0.03$ in this pedigree with a single crossover (individual IV-26 who is MRI positive and asymptomatic). Pedigree No. 2 was then screened with the D19S226 marker yielding a maximum lod score of 1.71 at $\theta=0.00$.

The combined data show a maximum lod score of 7.94 at $\theta=0.03$. A significant lod score ($Z_{max}=3.4$ at $\theta=0.00$) was also observed when only clinically affected members were analysed. Additional linkage data using four linked markers mapping to this region are shown in Table 1. The effects of assuming different allelic frequencies at the marker loci on the lod score results were also examined. The combined maximum lod scope for the two pedigrees was always greater than 6.65 when the highest allelic frequency was 0.8 or less. Based on clinical and neuroimaging data, penetrance was estimated to be complete above 35 years of age. However varying the penetrances down to 90% did not change the lod scores results significantly.

Multipoint Analysis

Figure 4:
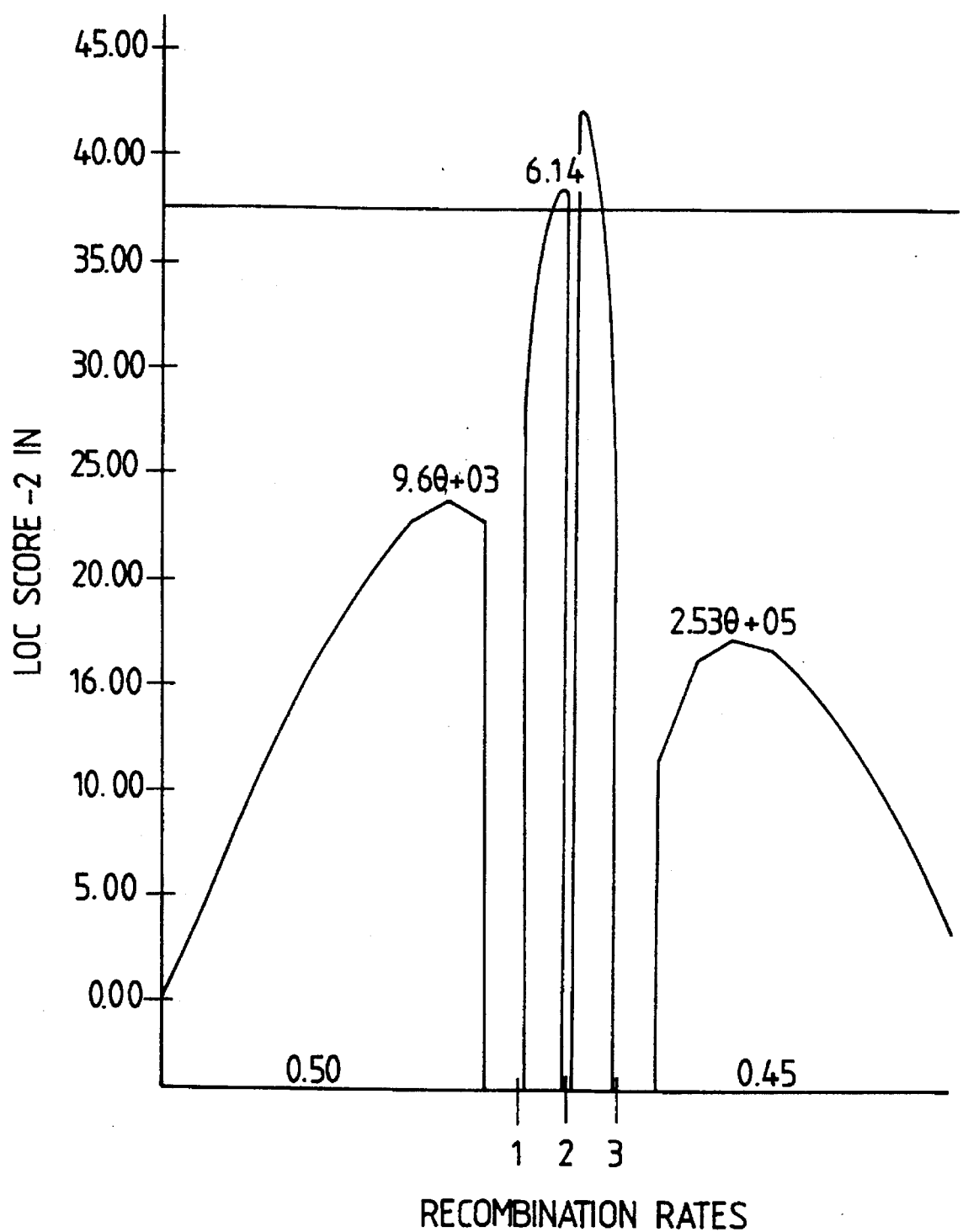
FIG. 4: Multipoint linkage analysis. Location scores for different positions of the CADASIL locus with respect to D19S221 (1), D19S226 (2) and D19S222 (3). The solid line indicates the 10:1 odds (1-lod-unit) interval for the locus. Odds against alternatives are shown for the most likely placements of CADASIL in each interval from the map.

Using the linked markers, multilocus analysis using location scores was used to establish the optimal gene order. The order D19S221-D19S226-D19S222 has previously been established with odds of over 1,000:1 by analysis of eight CEPH families. The sex-averaged recombination rates are approximately 0.07 in the interval defined by D19S221-D19S226 and 0.07 between D19S226-D19S222. Location score analysis based on this map showed that the CADASIL locus lies within the interval spanned by the two exterior markers with odds >9,000:1 (FIG. 4). Since significantly greater recombination was found in females compared to males in this region in the CEPH families (0.11 infemales versus 0.02 in males for D19S221-D19S226 and 0.15 in females versus 0.02 in males for D19S226-D19S222), location scores were also calculated with sex-differences in recombination rates. The results were comparable to those shown for the sex-average map.

Figure 5:
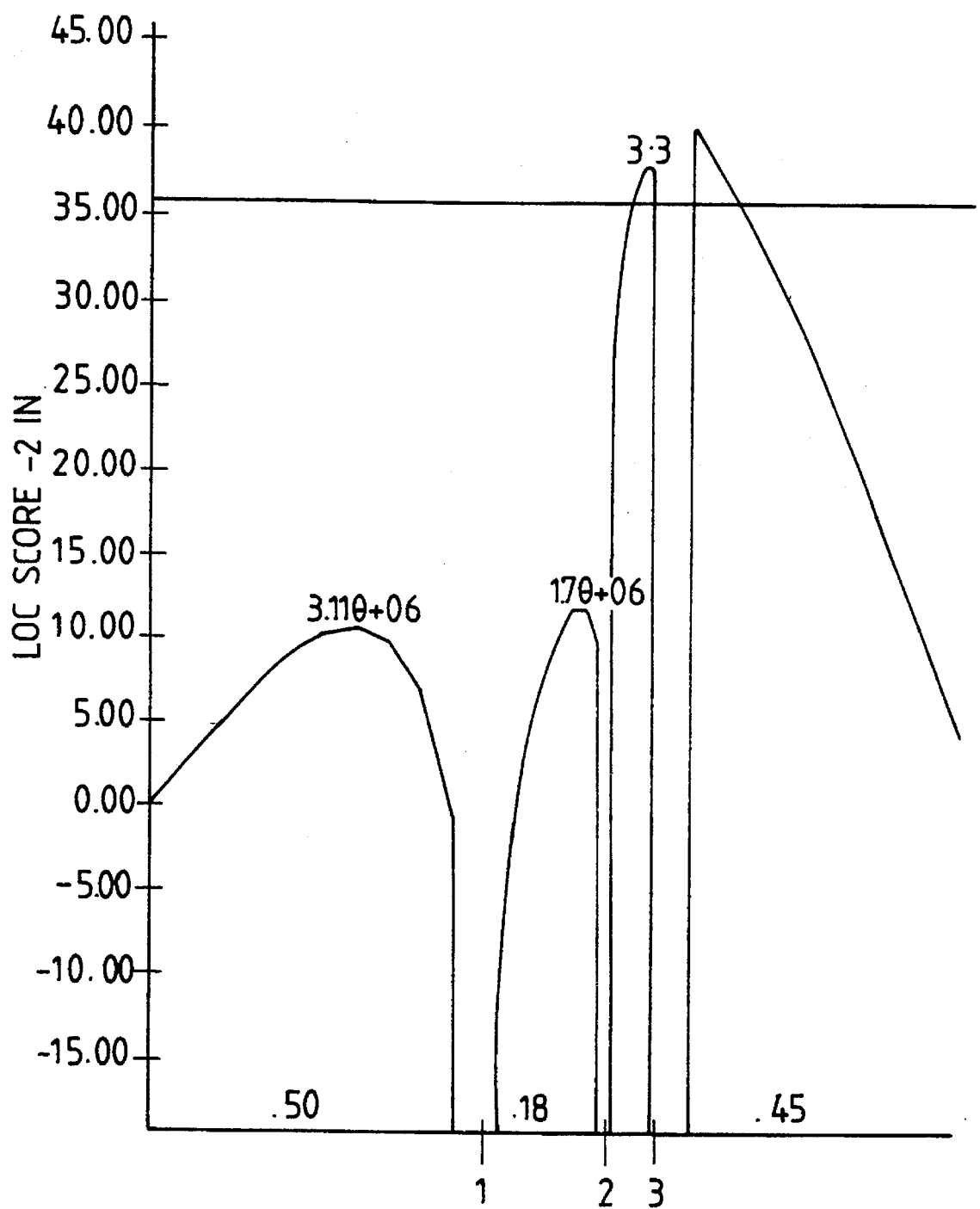
FIG. 5: Multipoint linkage analysis. Location scores for the CADASIL locus with respect to D19S216 (1), D19S221 (2) and D19S226 (3). The solid line indicates the 10:1 odds (1-lod-unit) interval for the placement of the locus. Odds against alternatives are shown for the most likely placements of CADASIL locus in each interval from the map.
Figure 6:
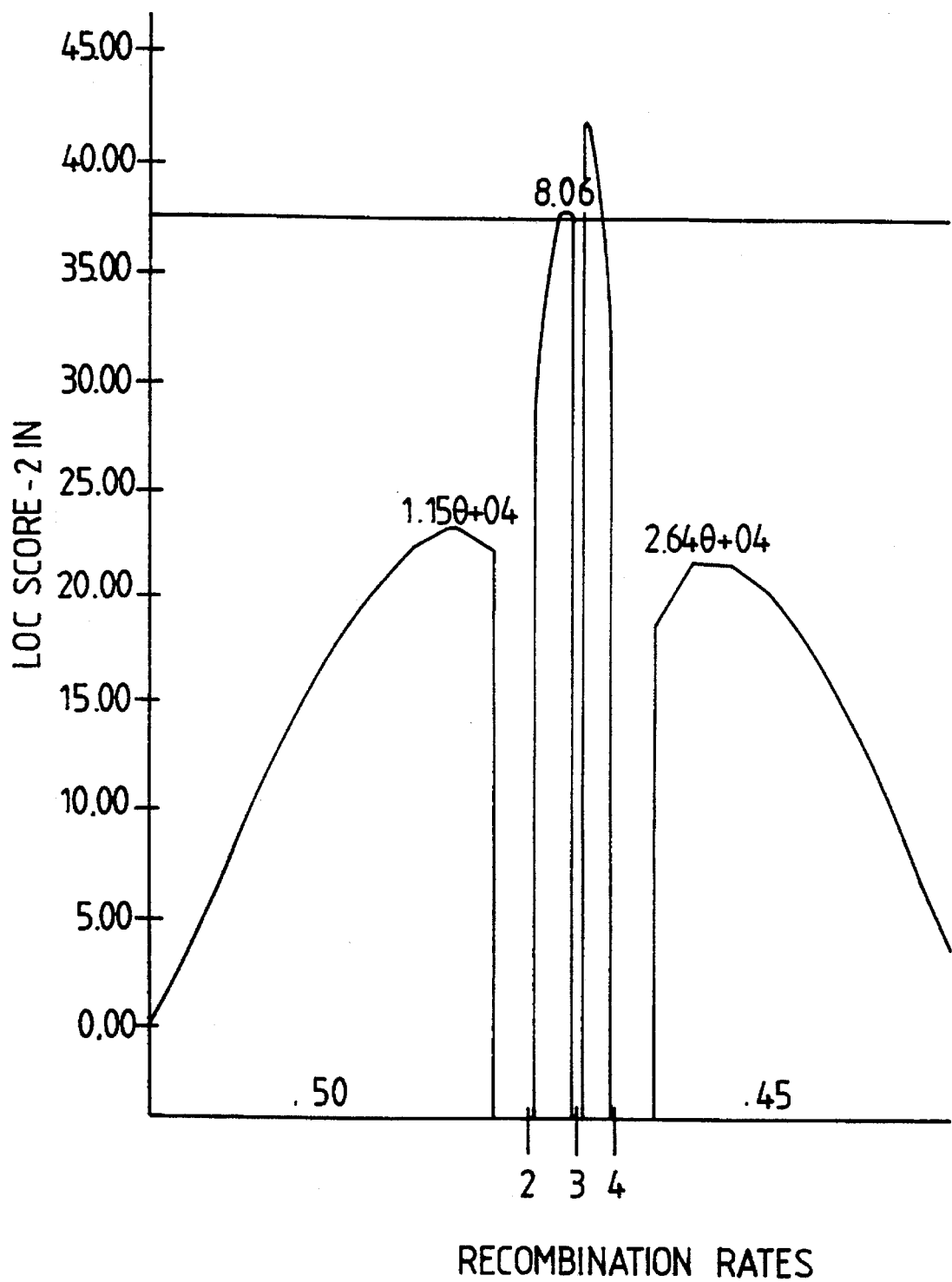
FIG. 6: analogous to FIG. 5, but with respect to D19S221 (2), D19S226 (3), and D19S215 (4).

Then, we reanalysed these four markers in the two CADASIL, families. Multilocus analysis confirmed that the CADASIL, locus maps to the interval D19S221-D19S215 (FIG. 5 and 6). Its most probable localisation is in the interval D19S226-D19S215. Examination of haplotypes in the CADASIL families revealed several recombination events leading to a rejection of the placement of the disease locus between D19S216 and D19S221; the odds against placement in this interval were greater than $10^6$:1 (FIG. 5). In contrast the interval D19S221-D19S226 could not be rejected (odds against this alternative were 8:1; FIG. 6).

Discussion

Using linkage analysis, the most likely location for the CADASIL gene was assigned between D19S221 and D19S215, with no evidence for heterogeneity.

Based on this study, MRI should be considered as a potentially useful tool in genetic linkage analysis of late onset diseases affecting the brain. Because of the assumption that the leukoencephalopathy could be present at an early stage of the disease, MRI was performed in all consenting adults above 25 years of age. This strategy allowed the identification of asymptomatic carriers. The disease status used for linkage analysis was then established on the cerebral MRI data, increasing the number of potentially informative meiosis and therefore shortening considerably the genome exclusion step. It also made possible the mapping using one pedigree, avoiding any complications of heterogeneity. The homogeneity of both pedigrees was then shown by the analysis of the second one.

Methodology

Markers. 111 markers containing short tracts of $(CA)_n$ repeats were chosen on the basis of the Genethon linkage map on the basis of their informativity and, when possible, at an average genetic distance of no more than $\theta=0.2$. All oligonucleotide sequences are available in the Genome Data Bank. The 25 VNTR minisatellites were originally isolated by Y. Nakamura, R. White and colleagues (personal communication).

PCR. Polymorphic genomic sequences were amplified by PCR using a PHC3Techne apparatus. The reactions were performed in a final volume of 50 µl containing 200 ng of genomic DNA, 125 µM 4 dNTP mix, 1×PCR Boehringer Taq polymerase buffer, 1 U Boehringer Taq Polymerase, 1 µM of each primer (oligonucleotides sequences). Samples were processed through 30 temperatures cycles (1st cycle, 94° C. for 5 min; 28 cycles including a denaturation step at 92° C. for 1 min, an annealing step at 55° C. for 1 min and an extension step at 72° C. for 1 min; the last cycle allowed extension at 72° C. for 10 min).

After addition of 75 µl of loading buffer the samples were denatured for 10 min at 94° C., then laid on a 6% acrylamide DNA sequencing gel. After blotting, nylon membranes were fixed in 0.4M sodium hydroxyde and hybridized with a (CA) 12 mer, $^{32}$P labelled probe for 14 h.

Linkage analysis. Two point and multipoint linkage analysis were performed using the LINKAGE package. Only individuals of defined status were analysed. Lod scores were calculated at various recombination fractions for each marker. The number of alleles of the 5 critical markers used for pairwise and multipoint linkage analysis, as well as their respective frequencies, were determined in the CEPH Caucasian reference families and are the following: D19S216 (AFM 164 zb8): 5 alleles, A (25%), B (30.5%), C (25%), D (14.2%), E (5.3%). D19S221 (AFM 224yc9); 10 alleles, A (23.2%), B (8.9%), C (8.9%), D (7.1%), H (7.1%), F (17.8%), G (10.7%), H (12.5%), I (1.7%), J (1.74%).

D19S226 (AFM 256yc9): 12 alleles, A (23.2%), B (10.7%), C (3.5%), D (8.9%), E (5.3%), F (23.2%), G (12.5%), H (1.7%), I (1.7%), J (5.3%), K (1.7%), L (1.76%). D19S222 (AFM 234vb2): 4 alleles, A (48.2%), B (28.5%), C (8.9%), D (14.22%). D19S208 (AFM 116xc7): 5 alleles, A (40.7%), B (27.7%), C (18.5%), D (9.2%), E (3.72%).

Protocol of the Diagnosis

The protocol which will be described hereinafter is given by way of example and as such is not considered as limitative. On the basis of the polymorphisms disclosed therein, all known methods of genotypic diagnosis are applicable.

Protocol

Obtaining DNA from the available family members whose status with respect to the disease is known; the nuclear DNA can, for example, be isolated from peripheral blood leucocytes, lymphoblastoid cell lines, cultured amniotic fluid cells, or chorionic villi, by standard proteinase K treatment and phenolchlorophorm extraction techniques, and amplified or digested with the appropriate restriction enzymes if needed.

Hybridizing the selected set of primers to the DNA. All oligonucleotide sequences serving as primers are available in the Genome Data Bank.

Amplifying the polymorphic alleles by the PCR technique, using advantageously an automatic thermocycler apparatus such as the PHC3 Techne apparatus. See for example paragraph "PCR" in Methodology. Analysing the size of the amplification products (amplimers), for example by electrophoresis on denaturating acrylamide DNA sequencing gel, blotting on Nylon membranes, hybridizing with radiolabelled suitable repeat probes.

Alternatively, restriction polymorphic fragments can be analysed on agarose gels after Southern blotting.

Data obtained from autoradiographs are computed and Lod-score calculations are carried out using the M-LINK program.

The assertion of linkage or absence of linkage is derived from statistical analysis, a Lod-score above 3 establishing unambiguous linkage of the disease gene to the tested marker. See above, a lod-score <−2 excluding linkage.

Determination of the most informative polymorphims (microsatellites) for the studied family.

When an at risk individual from an affected family is to be tested for predictive diagnosis, the protocol can be completed in the following manner:

Obtaining DNA from the individual in the same manner than above.

Hybridizing the selected set of primers to the DNA.

Amplifying as above.

Analyzing the amplification products as above.

Using linked polymorphic markers, a DNA based carrier risk can be calculated using the M-LINK program.

The same method can be used for prenatal carrier risk diagnosis.

TABLE 2

Pairwise linkage data for CADASIL

| Locus | | Recombination fraction | | | | | | Z max | θ |
|---|---|---|---|---|---|---|---|---|---|
| | | 0.00 | 0.05 | 0.10 | 0.20 | 0.30 | 0.40 | | |
| O19S216-AFM164zb8 | Family 1 | −99.00 | −2.14 | −0.55 | 0.43 | 0.44 | 0.03 | 0.52 | 0.24 |
| | Family 2 | −99.00 | 0.85 | 0.93 | 0.79 | 0.50 | 0.18 | 0.93 | 0.10 |
| | Total | −99.00 | −1.29 | 0.38 | 1.23 | 0.94 | 0.22 | 1.24 | 0.21 |
| O19S221-AFM224ye9 | Family 1 | −99.00 | 2.79 | 3.16 | 2.89 | 2.13 | 1.08 | 3.17 | 0.12 |
| | Family 2 | 2.53 | 2.39 | 2.13 | 1.60 | 1.03 | 0.44 | 2.63 | 0.00 |
| | Total | −99.00 | 5.18 | 5.29 | 4.50 | 3.16 | 1.52 | 5.33 | 0.09 |
| O19S226-AFM256yc9 | Family 1 | −99.00 | 6.30 | 5.93 | 4.79 | 3.36 | 1.67 | 6.34 | 0.03 |
| | Family 2 | 1.71 | 1.51 | 1.32 | 0.92 | 0.52 | 0.16 | 1.71 | 0.00 |
| | Total | −99.00 | 7.82 | 7.25 | 5.71 | 3.88 | 1.83 | 7.94 | 0.03 |
| O19S222-AFM234vb2 | Family 1 | −99.00 | 0.81 | 1.52 | 1.58 | 1.26 | 0.55 | 1.72 | 0.16 |
| | Family 2 | −99.00 | −0.48 | −0.07 | 0.15 | 0.12 | 0.03 | 0.16 | 0.22 |
| | Total | −99.00 | 0.32 | 1.45 | 1.83 | 1.38 | 0.58 | 1.85 | 0.18 |
| O19S208-AFM116xc7 | Family 7 | −99.00 | −1.11 | 0.21 | 0.98 | 0.91 | 0.46 | 1.02 | 0.23 |
| | Family 2 | −99.00 | 0.90 | 0.98 | 0.83 | 0.55 | 0.24 | 0.98 | 0.10 |
| | Total | −99.00 | −0.21 | 1.19 | 1.82 | 1.46 | 0.71 | 1.82 | 0.20 |

We claim:

1. Method for the genotypic diagnosis of the presence of a mutated gene causing cerebral autosomal dominant arteriopathy with subcortical infarcts and leukoencephalopathy (CADASIL) in symptomatic or at risk individuals or fetuses belonging to a family suspected of carrying said mutated gene comprising:

a) detecting the presence or absence of DNA polymorphisms genetically linked to the mutated gene causing CADASIL wherein said polymorphisms are located in the genetic interval of chromosome 19 flanked by and including the polymorphic microsatellite markers D19S221 and D19S215;

b) determining the risk to the individual or fetus of carrying said mutated gene based on the presence or absence of said polymorphisms thereby providing a genotypic diagnosis for CADASIL.

2. The method according to claim 1, wherein the DNA polymorphisms are microsatellite polymorphisms.

3. The method according to claim 2, wherein the microsatellites are selected from the group consisting of:

D19S221, D19S179, D19S226, D19S252, D19S253, D19S244, D19S415, D19S199, D19S215.

4. The method according to claim 1 wherein the detecting step (a) further comprises:
   (i) obtaining DNA from a symptomatic or at risk individual or fetus to be tested;
   (ii) contacting said DNA with primer pairs which specifically hybridize to sequences immediately flanking the microsatellite markers linked to the mutated gene causing CADASIL;
   (iii) amplifying said DNA to produce amplified sequences which include said microsatellite markers;
   (iv) analyzing the amplified sequences produced in step (iii) to determine the presence or absence of microsatellite polymorphisms genetically linked to the mutated gene by comparing said amplified sequences to amplified sequences produced when DNA from individuals of the same family and known to carry or not to carry a mutated gene causing CADASIL is tested;
and wherein step (b) further comprises determining the risk to said symptomatic or at risk individual or fetus based on the comparison of step (iv).

5. The method according to claim 4 wherein the comparison of amplified sequences is a size comparison.

6. A method for identifying the presence or absence of polymorphisms genetically linked to the mutated gene causing CADASIL comprising:
   (a) isolating DNA from individuals affected by CADASIL and from individuals who are not affected, symptomatic or at risk for CADASIL;
   (b) hybridizing DNA from said individuals with DNA probes which specifically hybridize to sequences in the genetic interval flanked by and including the microsatellite markers selected from the group consisting of D19S221, D19S179, D19S226, D19S252, D19S253, D19S244, D19S415, D19S199, D19S215;
   (c) comparing hybridization patterns of said DNA probes as a means of identifying polymorphisms;
   (d) determining the genetic linkage of these polymorphisms to said microsatellite markers.

* * * * *